(12) United States Patent
Bendix et al.

(10) Patent No.: US 11,399,973 B2
(45) Date of Patent: Aug. 2, 2022

(54) WASTE COLLECTION BAG

(71) Applicant: Coloplast A/S, Humlebaek (DK)

(72) Inventors: Jakob Bendix, Copenhagen (DK); Hans Falleboe, Gentofte (DK); Marcus Hoggarth, London (GB); Jeanne Marell, London (GB)

(73) Assignee: Coloplast A/S, Humlebaek (DK)

( * ) Notice: Subject to any disclaimer, the term of this patent is extended or adjusted under 35 U.S.C. 154(b) by 951 days.

(21) Appl. No.: 16/105,985

(22) Filed: Aug. 21, 2018

(65) Prior Publication Data

US 2018/0353317 A1 Dec. 13, 2018

Related U.S. Application Data

(63) Continuation of application No. 14/343,272, filed as application No. PCT/DK2012/050344 on Sep. 14, 2012, now Pat. No. 10,076,438.

(30) Foreign Application Priority Data

Sep. 14, 2011 (DK) .............................. PA 2011 70505

(51) Int. Cl.
*A61F 5/44* (2006.01)
*A61F 5/448* (2006.01)
*A61F 5/445* (2006.01)
*A61F 5/443* (2006.01)

(52) U.S. Cl.
CPC ............ *A61F 5/4404* (2013.01); *A61F 5/443* (2013.01); *A61F 5/445* (2013.01); *A61F 5/448* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,570,490 A * | 3/1971 | Berger | ..................... | A61F 5/445 604/339 |
| 3,712,304 A * | 1/1973 | Marsan | ................... | A61L 24/08 604/336 |
| 3,941,133 A * | 3/1976 | Chen | ...................... | A61F 5/443 604/336 |
| 4,786,283 A * | 11/1988 | Andersson | .............. | A61F 5/448 604/338 |
| 4,981,465 A * | 1/1991 | Ballan | .................. | A61F 2/0009 600/32 |
| 5,769,831 A * | 6/1998 | Freeman | ................. | A61F 5/445 604/338 |
| 6,066,120 A * | 5/2000 | Whiteside | ............... | B32B 27/08 604/332 |
| 6,135,986 A | 10/2000 | Leisner et al. | | |
| 8,657,799 B2 * | 2/2014 | Carrubba | ................ | A61F 5/445 604/318 |
| 8,845,606 B2 * | 9/2014 | Nguyen-Demary | .... | A61F 5/448 604/338 |
| 9,283,735 B2 * | 3/2016 | Pham | ..................... | B32B 27/32 |
| 9,943,436 B2 * | 4/2018 | Nguyen-Demary | .... | A61F 5/445 |
| 10,076,438 B2 * | 9/2018 | Bendix | .................... | A61F 5/443 |
| 2002/0064614 A1 * | 5/2002 | Turnbull | ................. | B32B 27/08 428/35.4 |
| 2005/0261645 A1 * | 11/2005 | Conrad | .................... | A61F 5/445 604/332 |
| 2006/0228318 A1 * | 10/2006 | Fabo | ....................... | A61F 5/445 424/70.12 |
| 2008/0154220 A1 * | 6/2008 | Gaffney | .................. | A61F 5/445 604/339 |
| 2008/0269699 A1 * | 10/2008 | O'Toole | ................... | A61F 5/448 604/332 |
| 2008/0269700 A1 * | 10/2008 | O'Toole | ................ | A61F 5/4405 604/332 |
| 2009/0234312 A1 * | 9/2009 | O'Toole | ................... | A61F 5/448 604/332 |
| 2011/0028924 A1 | 2/2011 | Murray | | |
| 2012/0179124 A1 * | 7/2012 | Nguyen-Demary | .... | A61F 5/448 604/335 |
| 2013/0035653 A1 * | 2/2013 | Kannankeril | ........... | A61F 5/445 493/267 |
| 2013/0116636 A1 * | 5/2013 | Carrubba | ................ | A61F 5/448 604/318 |
| 2013/0156983 A1 * | 6/2013 | Pham | ..................... | B32B 27/18 428/36.7 |
| 2014/0296807 A1 * | 10/2014 | Bendix | .................... | A61F 5/443 604/332 |
| 2018/0353317 A1 * | 12/2018 | Bendix | ................. | A61F 5/4404 |

FOREIGN PATENT DOCUMENTS

| CN | 1230137 C | 12/2005 |
|---|---|---|
| EP | 1018325 A1 | 7/2000 |
| WO | 2013037378 A1 | 3/2013 |

* cited by examiner

*Primary Examiner* — Guy K Townsend
(74) *Attorney, Agent, or Firm* — Coloplast Corp., Coloplast A/S; Nick Baumann

(57) ABSTRACT

A waste collection bag adapted for use by a person having a colostomy, an ileostomy, or a urostomy. The waste collection bag has a rear wall, a front wall on an opposite side of the waste collection bag from the rear wall, and a waste inlet formed in the rear wall of the waste collection bag. The waste inlet sized to fit around a stoma that has been formed through skin of the person. At least the front wall of the waste collection bag has a wall color characterized by a color value measured by a CMYK color code system, where the color value is in a range of: M from 0 to 15; Y from 0 to 10; and K from 10 to 25.

17 Claims, No Drawings ically gray with a tint of color and may be defined by the
CMYK value of e.g. cyan blue and yellow together with
black.

WASTE COLLECTION BAG

FIELD OF THE INVENTION

This invention relates to a human waste collection bag, especially a collection bag being suitable for a colostomy, an ileostomy or a urostomy, being capable of appearing less visible under clothes when worn by a user.

BACKGROUND OF THE INVENTION

When having to wear a stoma bag or other kind of human waste collection bag it is important for the patient that the bag is as discrete as possible. The ostomy bag is placed onto the patients skin and underneath the clothes.

Current ostomy appliances are typically provided with a pink skin color in order to simulate Caucasian flesh tone. The visual appearance of such devices is quite "clinical".

But people have different skin tone, and even the same person may change skin tone, by being tanned by the sun. Therefore, the pink skin colored bag will never blend in with the skin. Especially, when working with darker skin tones the pink skin colored bag may form a glaring contrast to the skin, rendering the bag clearly visible when wearing light-colored and/or semi-transparent clothes.

Ostomy bags are only made in one color, the pink skin color which is supposed to fit all the costumers. But patient's skin tones take many colors as does the clothes on top of the skin and bag. It is therefore difficult to match the exact right color of the bag that provides small contrast to the skin tone of the user thereby being discrete underneath e.g. a white shirt. The problem is commonly solved by making the ostomy bag in a pink skin tone, thereby imitating the skin, and always in Caucasian skin colors. The pink skin color of current designs will only match the skin of very few of the users and is therefore an unsuccessful attempt to hide the ostomy bag by matching the user's skin color.

Thus, there is a need to provide a collection bag being capable of blending in with different skin tones and being discrete under the clothes.

SUMMARY OF THE INVENTION

The present disclosure reveals that having a particular grayish color, the ostomy bag becomes less visible under a thin piece of garment than bags of traditional color. For a particular narrow range of grayish color, the bag was almost invisible.

In a first aspect, the present invention relates to a collection bag that is able to change the visual appearance of the bag in terms of color to visually make it appear like a fashion accessory or other common object thereby reducing the stress of the user who might otherwise be embarrassed by the appearance of the medical appliance.

In a second aspect, the present invention relates to a collection bag being discrete to wear, being less visible under the clothes.

In a third aspect, the invention relates to a collection bag having a color being less discriminating to users with dark skin but still fit to users with pale (Caucasian) skin.

DETAILED DESCRIPTION OF THE INVENTION

The present invention relates to a human waste collection bag, being suitable for a colostomy, an ileostomy or a urostomy, comprising a front wall facing away from the skin and a rear wall facing towards the skin, the front and rear walls being made from flexible material, the bag having an inlet opening for receiving human waste, wherein at least the front wall has a color with a value in the range of $L^*=60.0$ to $80.0$, $a^*=-1.5$ to $+2.0$ and $b^*=+1.5$ to $+9.0$ measured in the CIE $L^*a^*b^*$ color code system as described herein.

The color of the bag is a selected range of gray or grayish colors that has been shown to be less visible under clothes. On visual inspection they also show low contrast to the skin. The color range of the collection bag of the invention has been carefully selected in order to provide the smoothest contrast to any skin color of the users of both Caucasian and African origin. Colors in this range may appear discrete on the skin as the contrast is low as well as they may be substantially invisible when worn under light-colored and/or semi-transparent clothes.

The selected color range appears as gray or gray with a tint of color. It has surprisingly been shown that the selected gray color, contrary to the pink skin color will appear very discrete or invisible when worn under clothes and is capable of blending in with a broad spectrum of skin colors.

The color may be pure gray, i.e. a mixture of black and white or it may contain a color shade. The color shade may be warm, e.g. red or yellow or it may be cold, such as green, blue or violet.

Measured in the CMYK color code system, at least the front wall may have a color in the range $K=10-25$ as defined in the CMYK color code model.

The front wall of the bag may have a color in at least one of the ranges $C,M,Y,K=\{0;0;0;10-25\}$, $\{0-5;0;0;10-25\}$, $\{0-5;0;0-5;10-25\}$, $\{0-10;0-5;0;10-25\}$, $\{0;0-15;0-10;10-25\}$, $\{0;0-5;0-10;10-25\}$ and $\{0;0;0-5;10-25\}$ in the CMYK color code model.

The codes in the CMYK color code model for the various colors are shown in Table 1. In the CMYK color code model, the "C" is Cyan Blue, the "M" is Magenta Red and "Y" is Yellow. These three colors are called the primary colors, as all colors can be mixed from these. The "K" value is an expression for the gray tone of the color, the amount of black in the color.

TABLE 1

| Bag color | | C | M | Y | K |
|---|---|---|---|---|---|
| Neutral (pure gray) | | | | | 10-25 |
| Cold | Blue | 0-5 | | | 10-25 |
| | Green | 0-5 | | 0-5 | 10-25 |
| | Violet | 0-10 | 0-5 | | 10-25 |
| Warm | Red | | 0-15 | 0-10 | 10-25 |
| | Orange | | 0-5 | 0-10 | 10-25 |
| | Yellow | | | 0-5 | 10-25 |

As it appears from Table 1, a cold tinted gray color may be achieved by adding an amount of blue, green or violet to the gray color. The overall visual appearance of the bag is still gray, but the color has a cold glow. In the same way, a warm tinted gray color may be achieved by adding red, orange or yellow to the gray color.

A gray color can be achieved by diluting black until the desired gray value is obtained. However, a gray color may also be achieved by a mixing of blue, red and yellow in the right proportions, due to the fact that mixing complementary colors, e.g. red and green, the colors may eliminate each other's and the resulting color being black or gray. A gray produced in this way may also be defined by it K value, but may appear more vibrant to the spectator due to its complexity, a phenomenon well known by artists.

The color of the bag of the invention may be measured in the CIE L*a*b* color code system and have a value of L*=60.0 to 80.0, a*=−1.5 to +2.0 and b*=+1.5 to +9.0. As show in the examples they decrease the visibility from 8 to less than 6.6 on the used visibility scale. In a more preferred embodiment at least the front wall has a color value L*=60.0 to 80.0, a*=−1.5 to +2.0 and b*=+2.0 to +5.0, measured by the method described herein. For these colors, the bag has even lower visibility.

Whereas the current pink skin color used for collection bags typically is brighter than the skin, the color of the bag of the invention may typically have the same value or being slightly darker than the skin. The pink skin color is quite pale and is probably chosen in order to appear more delicate as a darker hue of the pink skin color may look a bit dirty and even more "clinical". The gray color with a value close to or darker than the color of the skin may more easily blend in with the skin of the user.

The gray color will appear less visible when seen through clothes such as a white shirt, as shown in the examples herein. Furthermore, also as illustrated, the grayish color appears less visible on a range of skin colors.

The gray or grayish color does not appear as a medical device or "clinical" which is important for the user as they usually prefer to be discrete about their health condition and need for a collection bag. The color may be pure gray or it may be tinted with another color such as yellow, blue or red or mixtures thereof as shown in Table 1. The amount of added color is low and leaves an overall impression of the color to be shades of gray.

The color may be tinted into a warm shade of gray, e.g. by adding a tint of red and/or yellow. The warm tone may provide a good match to a warm skin color.

Or the color may be tinted into a more cold shade of gray, e.g. by adding a tint of green, blue or violet. Such color may look more exclusive and be attractive to the user.

In the selection of a color that promotes the invisibility of an ostomy bag it is not only the ability of the color to blend in with the skin that determines the optimal color.

It occurs that there are more features that influence the invisibility of the bag. When the ostomy bag is mounted on the stomach of a standing person, the bag will not lie flat against the body but will, due to gravity, be located a distance from the skin. This effect will be even more pronounced when the bag is filled and enters a more three dimensional configuration. A subject mounted in a distance from another will throw a shadow, thus the bag will throw a shadow surrounding the bag on the skin.

Furthermore, when the bag is lying directly against the clothes of the user there will typically be space between the shirt and the skin of the user—but not between the bag and the clothes. This distance may result in a difference in the light reflected from the skin versus the light reflected from the bag, thereby making the contrast between the skin and the bag more distinct.

Studying shadows, these are usually not the same color as the subject throwing them; on the contrary, they are "cold" colors being the complementary color of the light source. Typically, the shadow color is in the gray-blue-violet. The pink skin color can be considered as a diluted orange (yellow-red mixture), being complementary to the shadow color. The contrast between complementary colors is high and thus more visible. The shadow of the ostomy bag may appear as a rather sharp dark outline encircling the bag and thereby accentuate the contour of the bag, rendering it more visible.

Moreover, the clothes of the user may also have an impact on the shadows by throwing a shadow towards the bag and skin.

Surprisingly, it has occurred that including some of the shadow color in the color of the bag may smoothen the sharp transition between the shadow outline and the bag, thereby masking the bag more effectively.

Mixing the shadow color (blue-violet) and the pink skin color (red-yellow) results in a gray or grayish color (by grayish is meant a grey with a tint of color such as disclosed in Table 1). The gray color has been shown to be more invisible under the clothes, blending in with the shades and with the skin when seen through a piece of fabric or textile.

The collecting bag itself comprises front and rear walls sealed together along the rim and is provided with an inlet opening. The bag may be made in analogy with and from materials conventionally used for preparation of disposable ostomy and wound and incontinence devices.

Such materials are suitably films composed of any suitable material which is heat sealable and sufficiently impervious for unpleasant odors such as polyolefin films or combinations of such films, e.g. polyethylene or a coextrudate of polyethylene and polyvinylidene chloride.

The bag may be provided with an adhesive for attachment to the skin. In one embodiment the adhesive is in the form of an adhesive wafer. Such wafer may typically comprise a backing layer coated with an adhesive layer. The wafer may comprise an aperture for receiving a stoma or body opening. The bag may be an ostomy collection bag.

The bag may be detachable from the wafer or it may be integrated with the wafer. Such appliances may be two-piece or one-piece appliances. In both types of appliances, an adhesive wafer is attached to the wearers skin. In case of a one-piece appliance, a receiving member or bag is attached to the adhesive wafer. In case of a two-piece appliance, the adhesive wafer forms part of a body side member and a receiving bag is attached releasably to the body side ostomy member for receiving exudates from the stoma.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 91/01118 and WO 91/01119 or WO 94/18919 or matching flanges for adhesive connection of the type disclosed in U.S. Pat. No. 5,800,415.

In one embodiment the bag is provided with an outlet. The outlet facilitates the bag to be emptied and reused.

The bag may comprise walls having two or more layers such as an inner wall facing the inside of the bag and an outer wall (front and rear wall). The inner wall may be impermeable to moisture and odor in order to control the human waste (feces, urine) whereas the outer wall may serve as ornamental, securing a discrete appearance as well as it may provide a comfortable soft surface. Non-woven materials are often used for the outer wall as it is soft against the skin and discrete. It is preferred that at least the outer front wall is colored.

The inner walls may be the same color as the outer walls or they may be slightly darker. In one embodiment the inner walls are transparent or translucent.

The rear wall may preferably be provided with the same color as the front wall, thereby leaving the bag in plain grayish. This may be an advantage for the manufacturing of the bag as well as it may appear more aesthetical.

In contrast to known products, the color range does not attempt to blend in with the skin hue, but to the value of the skin. The gray color does not intend to imitate skin, but tries instead to lower the contrast between the skin and the bag and thereby making it less visible on every skin tone.

By introducing a skin neutral bag color the performance range is increased. The bag will fit various skin colors and therefore making it much more versatile.

METHODS

Visibility Test

The visibility of an ostomy bag was tested by a test panel of 10 persons performing a subjective visual test under conditions as close as possible to daily life conditions.

Flesh color is not a single definite color, but varies considerably dependant on the origin of the people, from very pale, over reddish, golden tan, olive to dark brown. In order to match a broad variety of skin tones, we prepared artificial skins in Caucasian and African skin colors for use for the test.

Color samples were mounted on the artificial skins and covered with a piece of white textile. White textile was chosen as white being the most sensitive color in an visibility test as it is bright and neutral as well as it often is transparent/translucent.

The test samples were viewed in daylight by the test panel, rating the samples with a character of 1-8, "8" being the most visible to "1" being the most invisible. The color of the test samples were determined by the CIE L*a*b* color code system and measured over a standard. The results from the test and the standard are shown in Table 2 below. The test shows that the gray color is more invisible than the pink skin color.

TABLE 2

| Sample | | CIE L*a*b* | | | Visibility | |
|---|---|---|---|---|---|---|
| No. | Color | L* | a* | b* | African skin | Caucasian skin |
| A | Pink skin | 72.49 | 6.23 | 12.53 | 8 | 8 |
| B | Beige gray | 68.04 | 1.23 | 4.29 | 3.3 | 1.9 |
| C | Pure gray | 64.71 | 0.60 | 3.05 | 2.1 | 1.4 |
| D | Warm gray | 74.15 | 0.85 | 3.50 | 6.4 | 6.4 |
| E | Light gray | 71.35 | −0.29 | −0.74 | 5.5 | 5.8 |
| F | Light green gray | 69.18 | 0.29 | 8.32 | 4.6 | 3.9 |
| G | Green gray | 63.49 | −0.99 | 2.83 | 1.3 | 2.8 |
| St. | Standard | 73.54 | 0.60 | 3.62 | — | — |

Determination of Color

A color may be defined in many ways. Two of the most recognized color systems are the CMYK color model and the CIE L*a*b* system. The color of the ostomy bag of the present invention has been determined by both methods.

CMYK Color Model

The color may be determined by visual comparison with color standards that are defined by the CMYK color model. The CMYK color model (process color, four color) is a subtractive color model, used in color printing, and is also used to describe the printing process itself. CMYK refers to the four inks used in some color printing: cyan, magenta, yellow, and key (black). The "K" in CMYK stands for key since in four-color printing cyan, magenta, and yellow printing plates are carefully keyed or aligned with the key of the black key plate.

CIE L*a*b* System

The color was determined using a spectrophotometer of the type Sphere d/8° Spectrophotometer for color measurements, type SP64 Series, Manufacturer: X-Rite. The settings were the following: Target window: 4 mm (size of measuring area), Light source D65/10°, Specular component SPIN (Specular component included—SCI. Non UV filter) and room temperature 22.5° C. Measured over black background. The colors were represented by (CIE) Colour Standards Committee Systems.

| L*: Lightness/Darkness (Value: 0-100) | White is 100 and black is 0. |
|---|---|
| a*: Red/Green coordinate | Positive value = Red, negative value = Green |
| b*: Yellow/Blue coordinate | Positive value = Yellow, negative value = Blue |
| h°: Hue (Value: 0-360°) | The hue angle indicates the color. |
| C*: Chroma (Value: 0-100) | Gray is 0 and 100 is a fully saturated color. |

Standard tolerance: $CMC_{2:1}$: L* = 2, h° = Variable ellipse, C = 1, Cf = 1 (Commercial factor expends ellipse).

What is claimed is:

1. A waste collection bag adapted for use by a person having a colostomy, an ileostomy, or a urostomy, the waste collection bag comprising:
   an inner rear wall, an inner front wall on an opposite side of the waste collection bag from the inner rear wall, and a waste inlet formed in the inner rear wall of the waste collection bag, with the waste inlet sized to fit around a stoma that has been formed through skin of the person;
   wherein the inner rear wall and the inner front wall are each formed of a film comprising one of a polyolefin and a polyvinylidene chloride, with the inner rear wall and the inner front wall are sealed together to form an inner bag that is configured to be impermeable to moisture and so adapted to contain human waste;
   an outer rear wall and an outer front wall disposed over the inner bag, with the outer front wall formed of a nonwoven material;
   wherein at least the nonwoven material of the outer front wall of the waste collection bag has a wall color characterized by a color value measured by a CMYK color code system, where the color value is in a range of:
   M from 0 to 15;
   Y from 0 to 10; and
   K from 10 to 25.

2. The waste collection bag of claim 1, wherein, when M=0 and Y=0, at least the nonwoven material of the outer front wall of the waste collection bag has the color value measured by the CMYK color code system of:
   C from 0 to 5; and
   K from 10 to 25.

3. The waste collection bag of claim 1, wherein, when M=0, at least the nonwoven material of the outer front wall of the waste collection bag has the color value measured by the CMYK color code system of:
   C from 0 to 5;
   Y from 0 to 5; and
   K from 10 to 25.

4. The waste collection bag of claim 1, wherein, when Y=0, at least the nonwoven material of the outer front wall of the waste collection bag has the color value measured by the CMYK color code system of:
   C from 0 to 10;
   M from 0 to 5; and
   K from 10 to 25.

5. The waste collection bag of claim 1, wherein the color value of the nonwoven material of the outer front wall is in a range of:
M from 0 to 5;
Y from 0 to 10; and
K from 10 to 25.

6. The waste collection bag of claim 1, wherein, when C=0 and M=0, at least the nonwoven material of the outer front wall of the waste collection bag has the color value measured by the CMYK color code system of:
Y from 0 to 5; and
K from 10 to 25.

7. The waste collection bag of claim 1, wherein the color value of the nonwoven material of the outer front wall is in a range of:
C=0;
M=0;
Y=0; and
K from 10 to 25.

8. The waste collection bag of claim 1, wherein at least the nonwoven material of the outer front wall of the waste collection bag consisting of the wall color as characterized by the color value range.

9. The waste collection bag of claim 1, wherein at least the nonwoven material of the outer front wall of the waste collection bag consisting essentially of the wall color as characterized by the color value range.

10. The waste collection bag of claim 1, wherein the outer rear wall is formed of the nonwoven material, and the nonwoven material of the outer rear wall of the waste collection bag has an identical color value as the front wall.

11. The waste collection bag of claim 1, further comprising an adhesive applied to the outer rear wall, with the adhesive adapted for attachment to the skin of the person.

12. The waste collection bag of claim 1, further comprising a wafer connected to the outer rear wall, where the wafer forms a hole that is sized to fit around the stoma, with the hole aligned with the waste inlet formed in the inner rear wall of the waste collection bag, and the wafer includes an adhesive for attachment of the wafer to the skin of the person.

13. The waste collection bag of claim 1, further comprising a wafer removably attachable to the outer rear wall, where the wafer forms a hole that is sized to fit around the stoma, with the hole aligned with the waste inlet formed in the inner rear wall of the waste collection bag, and the wafer includes an adhesive for attachment of the wafer to the skin of the person.

14. A waste collection bag adapted for use by a person having a colostomy, an ileostomy, or a urostomy, the waste collection bag comprising:
an inner rear wall, an inner front wall on an opposite side of the waste collection bag from the inner rear wall, and a waste inlet formed in the inner rear wall of the waste collection bag, with the waste inlet sized to fit around a stoma that has been formed through skin of the person, wherein the inner rear wall and the inner front wall are each formed of a film comprising one of a polyolefin and a polyvinylidene chloride, with the inner rear wall and the inner front wall sealed together to form an inner bag that is configured to be impermeable to moisture and so adapted to contain human waste;
an outer rear wall secured to an outer front wall to contain the inner bag, with both of the outer rear wall and the outer front wall formed of a nonwoven material;
wherein, when the waste collection bag is attached to the person, the nonwoven material of the outer rear wall is located a distance away from the skin of the person to form a shadow having a shadow color, and the nonwoven material of the outer front wall consisting of one wall color that is formulated to include the shadow color;
wherein the one wall color is configured to reduce contrast with the shadow color to allow the waste collection bag to be less visible, when viewed through clothing, than a visibility of a waste collection appliance having a skin tone color, when viewed through the clothing, where the skin tone color is characterized as L* of about 72; a* of about 6; and b* of about 12 measured by a CIE L*a*b* color code system.

15. The waste collection bag of claim 14, wherein the one wall color is formulated to include a blue shadow color and a violet shadow color.

16. A waste collection bag adapted for use by a person having a colostomy, an ileostomy, or a urostomy, the waste collection bag comprising:
a rear wall, a front wall on an opposite side of the waste collection bag from the rear wall, and a waste inlet formed in the rear wall of the waste collection bag, with the waste inlet sized to fit around a stoma that has been formed through skin of the person;
wherein at least the front wall of the waste collection bag has a wall color characterized by a color value measured by a CIE L*a*b* color code system, where the color value is in a range of:
L* from about 63 to about 68;
a* from negative 1.5 to positive 2.0; and
b* from positive 1.5 to positive 9.0.

17. The waste collection bag of claim 16, wherein the front wall of the waste collection bag is a nonwoven material.

* * * * *